(12) United States Patent
Huang et al.

(10) Patent No.: US 12,156,712 B2
(45) Date of Patent: Dec. 3, 2024

(54) UNIVERSAL ROBOT FOR INTERVENTIONAL ANGIOGRAPHIC SURGERY AND INTERVENTIONAL THERAPEUTIC SURGERY

(71) Applicant: BEIJING WEMED MEDICAL EQUIPMENT CO., LTD., Beijing (CN)

(72) Inventors: Tao Huang, Beijing (CN); Yan Li, Beijing (CN)

( * ) Notice: Subject to any disclaimer, the term of this patent is extended or adjusted under 35 U.S.C. 154(b) by 920 days.

(21) Appl. No.: 17/216,552

(22) Filed: Mar. 29, 2021

(65) Prior Publication Data

US 2022/0133422 A1    May 5, 2022

Related U.S. Application Data

(63) Continuation of application No. PCT/CN2021/073705, filed on Jan. 26, 2021.

(30) Foreign Application Priority Data

Oct. 29, 2020  (CN) .......................... 202011185437.9

(51) Int. Cl.
*A61B 34/00* (2016.01)
*A61B 34/30* (2016.01)
*B25J 9/10* (2006.01)

(52) U.S. Cl.
CPC .............. *A61B 34/71* (2016.02); *A61B 34/30* (2016.02); *B25J 9/1035* (2013.01); *A61B 2034/301* (2016.02); *A61B 2562/0252* (2013.01)

(58) Field of Classification Search
CPC ... A61B 34/71; A61B 34/30; A61B 2034/301; A61B 2562/0252; A61B 90/50; B25J 9/1035
See application file for complete search history.

(56) References Cited

U.S. PATENT DOCUMENTS

2009/0247942 A1* 10/2009 Kirschenman .... A61M 25/0147
604/95.04
2016/0271368 A1*  9/2016 Falb ................ A61M 25/09041

* cited by examiner

*Primary Examiner* — Eric F Winakur
*Assistant Examiner* — Abid A Mustansir

(57) ABSTRACT

The disclosure discloses a universal robot for interventional angiographic surgery and interventional therapeutic surgery. The robot meets the needs of both angiographic surgery and therapeutic surgery, which facilitates the clinical use. The robot is universal for both angiographic surgery and interventional therapeutic surgery, with advantages of simple structure, good stability, modular structure design, and so on, which is suitable for operation environment. By measuring the push and pull force of the micro force sensor at the driving end, the change of the axial friction force of the guide wire is judged, which gives the doctor timely reminder and protects the safety of patients. According to the feedback value of the high precision load cell at the driven end, the clamping degree of the guide wire is adjusted at any time to ensure there is no slipping phenomenon, which meets the needs of vascular interventional surgery.

10 Claims, 17 Drawing Sheets

UNIVERSAL ROBOT FOR INTERVENTIONAL ANGIOGRAPHIC SURGERY AND INTERVENTIONAL THERAPEUTIC SURGERY

CROSS-REFERENCE TO RELATED APPLICATIONS

This application is a continuation of International Patent Application No. PCT/CN2021/073705 with a filing date of Jan. 26, 2021, designating the United States, and further claims priority to Chinese Patent Application No. 202011185437.9 with a filing date of Oct. 29, 2020. The content of the aforementioned applications, including any intervening amendments thereto, are incorporated herein by reference.

TECHNICAL FIELD

The present disclosure relates to the technical field of minimally invasive vascular equipment, and more specifically, to a universal robot for interventional angiographic surgery and interventional therapeutic surgery.

BACKGROUND

The whole process of interventional surgery includes angiographic diagnosis, balloon dilatation, stent placement and other treatment processes. Among them, interventional angiography is the basis for the diagnosis of cardiovascular and cerebrovascular diseases, and also the premise for further treatment, while therapeutic surgery is a necessary step to relieve the pain. There are some differences in the operation methods and the realization processes of the two kinds of surgeries. In China, there are several problems in the robot of interventional angiography surgery: (1) the device is large in volume, complex in structure and low in stability, so it is not suitable for practical clinical surgery; (2) most robots have no force feedback system, which can not ensure the safety of surgery; (3) it is inconvenient to install and disassemble the system; (4) the disinfection process of robot is complicated, which does not meet the actual needs of surgery; (5) most robots can only perform interventional angiography or interventional therapy, and there is a lack of interventional robots that can complete angiography and therapy at the same time.

Therefore, it is an urgent problem for those skilled in the art to provide an interventional robot that can complete angiography and diagnosis at the same time.

SUMMARY

The disclosure aims to solve one of the above technical problems in the prior art at least to a certain extent.

Interventional angiographic surgery is the basis of diagnosis of cardiovascular and cerebrovascular diseases, and also the premise of further treatment. Interventional therapeutic surgery is a necessary step to relieve the pain. There are some differences in the procedure between interventional angiographic surgery and interventional therapeutic surgery. The disinfection box for interventional therapeutic surgery disclosed in the prior art can not be used for interventional angiographic surgery, because the angiographic surgery needs to control the rotation of the angiography catheter, so as to smoothly enter the coronary artery orifice and achieve the purpose of angiography. However, the existing disinfection box for interventional surgery can not rotate the catheter. Therefore, an object of the disclosure is to provide a universal robot for interventional angiographic surgery and interventional therapeutic surgery with a universal disinfection box, so as to solve the problem that in the prior art, the robot can only carry out interventional angiographic surgery or interventional therapeutic surgery, and lacks the interventional robot which can complete angiography and treatment at the same time.

The present disclosure provides a universal robot for interventional angiographic surgery and interventional therapeutic surgery, including a robot body. The robot body includes a base, a column and a mechanical arm. A top of the base is slidably connected with the column. A top of the column is connected with the mechanical arm. A front end of the mechanical arm is connected with a propulsion mechanism and a disinfection box. The front end of the mechanical arm supports the propulsion mechanism and the disinfection box.

The disinfection box includes a sterile box body and a sterile box cover hinged to one side of the sterile box body. A catheter drive assembly and a guide wire drive assembly are fixed on the sterile box body. A Y-valve assembly is provided on one end of the sterile box body. The Y-valve assembly includes a Y-valve fixing member, a Y-valve holding member, a Y-valve main body and a Y-valve drive gear.

One end of the Y-valve fixing member is rotated on one end of the sterile box body in an advancing direction of a catheter and a guide wire. Another end of the Y-valve fixing member is magnetically connected with the sterile box body. An engagement through hole is provided in the middle of the Y-valve fixing member. A shaft hole at a position corresponding to the engagement through hole is provided on the sterile box body. A bottom axle of the Y-valve drive gear is rotated in the shaft hole and the bottom of the axle is provided with an axle gear engaged with a motor output gear in a propulsion mechanism, The Y-valve drive gear is provided in the engagement through hole. The Y-valve holding member includes at least two sets of arc-shaped members connectable as a ring. A toothed ring meshed with Y-valve drive gear is provided on the ring. One end of the Y-valve main body is fixed in Y-valve holding member through an elastic filler, and another end of the Y-valve main body is fixed on the Y-valve fixing member.

According to the above technical solution, compared with the prior art, the present disclosure discloses a universal robot for interventional angiographic surgery and interventional therapeutic surgery with a changed structure of the Y-valve assembly thereof. Specially:

First, one end of Y-valve main body is fixed in the Y-valve holding member through an elastic filter. Through the deformation of the elastic filler, different specifications of the Y valve body can be used, so that different specification of the catheter or contrast catheter can be installed.

Second, the Y-valve driving gear is driven by the motor output gear in the propulsion mechanism, and the toothed ring on the Y-valve holding member can be driven at the same time, thus a universality of the interventional radiology and therapeutic operation disinfection box is realized.

Third, one end of a Y-valve fixing member is rotated on one side of the sterile box body in an advancing direction along a catheter and a guide wire, and the other end of the Y-valve fixing member is magnetically connected with the sterile box body, which allows the physician to replace the guide wire and catheter and fix the Y-valve main body.

Further, the Y-valve fixing member includes a fixing plate, an engaging ring body, a hinge and a claw. The fixing plate is bar shaped. A bottom of one end of the fixing plate is magnetically connected with the sterile box body. The other end of the fixing plate is integrally connected with one end of the engaging ring body. The engagement through hole is formed in the middle of the engaging ring body. The other end of the engagement ring body is connected with the hinge. The hinge is hinged with a hinge block provided on the sterile box body near an outside of the shaft hole. At least two sets of the claw are sequentially arranged along a longitudinal direction of the fixing plate. The other end of the Y-valve main body is engaged with the claw. The claw has certain elasticity, and an opening is formed at the top of the claw, which is convenient for installation and disassembly. A first Y-valve electromagnet near an inner side of the shaft hole is provided on the sterile box body. The first Y-valve electromagnet is magnetically connected with a second Y-valve electromagnet corresponding to a bottom position of the fixing plate, which thereby facilitating the fixation of the Y-valve main body.

A second object of the present disclosure is to provide a universal robot for interventional angiographic surgery and interventional therapeutic surgery with the base including a column bottom plate, a stopper, a cross brace, a base rail, a base slider, and a rack. The stoppers are fixed on the column bottom plate. The cross braces are fixed with the stopper and placed on a catheter bed. A top of the column bottom plate is fixed with the rack arranged along a length direction of the column bottom plate. Two groups of the base rails are symmetrically arranged on both sides of the rack, and each group of the base rails is slidably connected with the base sliders. A bottom of the column is provided with a connecting plate. A bottom of the connecting plate is fixed on the base sliders, and a top of the connecting plate is fixed with a base servo motor. An output end of the base servo motor is provided with a base gear meshing with the rack. The base servo motor drives the base gear and rack, and the column drives the mechanical arm and the propulsion mechanism to do translation motion, so as to drive the whole propulsion mechanism to move forward or backward. The imaging catheter is installed on the propulsion mechanism. The whole movement will drive the catheter into or out of the patient body, and then complete the process of angiography. Therefore, the reciprocating structure is adopted to reduce the space occupied by the operation of the equipment, which achieves the same effect as the doctor's actual interventional operation in a very small volume.

The stoppers also play the role of mechanical limit, which is used by matching with the connecting plate.

Further, a side of the column bottom plate close to the cross brace is provided with a sliding groove for inserting into a side guide rail of the catheter bed. There are tension screws at the bottom of the sliding groove for fixing. The bottom plate of the column is also provided with a wiring socket, which is used for connecting the power line and the communication line.

The two cross braces of the column can be placed on the catheter bed plate. The two cross braces, together with the sliding groove of the guide rail fixed on the catheter bed of the column, form a group of triangular stable structure. Thus, the stable connection between the mechanical arm and the catheter bed is ensured. The height of the column of the mechanical arm is appropriate, which ensures that it will not touch the patient and will not be too far away from the patient.

Further, the mechanical arm includes a rear arm, a middle arm and a forearm rotationally connected in turn. One end of the rear arm is rotationally connected to a top of the column. A front end of the forearm is connected with the propulsion mechanism and the disinfection box. The front end of the forearm supports the propulsion mechanism and the disinfection box. Each above rotating connection is provided with an annular indicator light respectively. The annular indicator lights display different colors according to different signals sent by the robot control circuit to feed back different state information of the robot. The mechanical arm is made of aluminum alloy, which is strong and light. The three straight arms are made of hollow aluminum profiles, which greatly reduces the weight of the mechanical arm.

Further, the rear arm and the middle arm have a same structure, and both include a transverse shaft, a first rotating shaft connecting assembly, a rotating shaft fixing assembly and a first rotating shaft. The first rotating shaft connecting assembly includes a first rotating shaft connector, a first lubricating block, a first bracket, a first thread pressing cover and a first shaft sleeve. One end of the first rotating shaft connector is fixed with one end of the transverse shaft. A groove is formed on the first rotating shaft connector to accommodate the first lubricating block. The first shaft sleeve penetrates through the through hole in the middle of the first s rotating haft connector and the first lubricating block. Two first brackets for installing the annular indicator lights are symmetrically fixed on both sides of the first rotating shaft connector. The first thread pressing cover is fixed on the first rotating shaft connector for fixing cables; the rotating shaft fixing assembly includes a rotating shaft fixing part, a wire pressing plate, a transverse shaft limiting part, a retaining ring and a T-type thrust gasket. One end of the rotating shaft fixing part forms a vertically arranged boss to fix the other end of the transverse shaft. The boss is far away from the transverse shaft to form a shaft installation area vertically arranged with the boss. The shaft installation area is provided with the first rotating shaft through bolts. The T-type thrust gasket is arranged between a top of the fixing seat of the first rotating shaft and a matched group of the first shaft sleeves. A top of the T-type thrust gasket is fixed by the retaining ring. A top of the rotating shaft fixing part is provided with the wire pressing plate for fixing the cables. Two groups of the transverse shaft limiting parts provided on both sides of the rotating shaft fixing part and a limiting screw provided at a bottom of the first rotating shaft connector matched with the transverse shaft limiting parts form a stop mechanism for limiting the rotation of the transverse shaft.

Further, the forearm includes a front transverse plate, a driver, an inclined vertical plate, a second rotating shaft connecting assembly, a forearm connecting shaft assembly and a second rotating shaft. A top of the front transverse plate is fixed with the driver for driving a stepper motor in the propulsion mechanism, and one end of the front transverse plate is fixedly connected with the second rotating shaft connecting assembly through the inclined vertical plate. The second shaft connecting assembly is internally connected with the first rotating shaft. The other end of the front transverse plate is fixed with the forearm connecting shaft assembly. The second rotating shaft is matched with the forearm connecting shaft assembly and fixed on the propulsion mechanism.

Further, the second shaft connecting assembly includes a second rotating shaft connector, a second lubricating block, a second shaft sleeve and a second bracket. One end of the second rotating shaft connector is fixed on a top of the inclined vertical plate by a screw, and a holding groove is formed inside the second shaft connector for holding the second lubricating block. The second shaft sleeve penetrates through the through hole in the middle of the second rotating shaft connector and the second lubricating block. Two second brackets are fixed on both sides of the second rotating shaft connector for installing an annular indicator light. The forearm connecting shaft assembly includes a shaft support, a third lubricating block, a flange bearing, a washer and a second rotating shaft retaining ring. The shaft support is fixed on the front transverse plate. The third lubricating block is fixed on one side of the shaft support. The second rotating shaft is fixed on a side wall of the propulsion mechanism. The second rotating shaft, the washer, the flange bearing and the second rotating shaft retaining ring are matched and installed on the shaft support, so that the propulsion mechanism rotates along the shaft support.

Further, the propulsion mechanism includes a shell, a guide wire driving end, a guide wire driven end and a catheter control end. One side of the shell is rotationally connected with the mechanical arm. An inner part of the shell is used to support and accommodate a guide wire driving end, a guide wire driven end and a catheter control end. The disinfection box is magnetically connected with a top of the shell. A top of the catheter control end penetrates into the disinfection box. The guide wire driving end and the guide wire driven end are symmetrically arranged along the guide wire. A side of the guide wire driving end close to the guide wire and a side of the guide wire driven end close to the guide wire are connected with two groups of matching guide wire rolling parts respectively.

Further, the guide wire driving end includes a driving end connecting plate and two groups of driving end parts. Each set of the driving end part includes a U-shaped slot connector, a driving end high precision load cell, a first slider, a first micro linear guide, a right-angle connecting plate and a driving end connecting piece. A top of the driving end connecting piece slides along a direction parallel to the guide wire on a length direction of the driving end connecting plate. A bottom of the right-angle connecting plate slides perpendicularly to the direction of the guide wire on the top of the driving end connecting piece. An outside of a vertical plate connected on one end of the right-angle connecting plate is butted with a camshaft, and a top of the other end is fixed with the first micro linear guide parallel to the direction of the guide wire. The first slider slides on the first micro linear guide, and the U-shaped slot connector is fixed on the top of the first slider to counteract a clamping force of the guide wire. The driving end high precision load cell is arranged perpendicularly to the guide wire. One end of the driving end high precision load cell is fixed on an inner side of the vertical plate, and the other end is inserted into a notch of the U-shaped slot connector, and a width of the notch is greater than a width of the driving end high precision load cell. The high precision load cell is used to measure a friction on the guide wire. A side far away from the notch of the U-shaped slot connector is fixed with one end of a first clamping part.

The guide wire driven end includes a driven end connecting plate, a driven end high precision load cell, a driven end micro linear guide, a driven end slider, a driven end connecting piece and two groups of passive rolling parts. A side surface of the driven end connecting plate close to the guide wire is fixed with the driven end high precision load cell. A top of the driven end connecting plate is fixed with the driven end micro linear guide. Two driven end connecting piece are fixed on the tops of the two driven end sliders and slide on the driven end micro linear guide. A top of each driven end connecting piece is fixedly provided with the passive rolling part matched with an active rolling part of the guide wire driving end respectively. The driven end high precision load cell transmits a force change signal received in the process of rolling and clamping to a control end of the driving end of the propulsion mechanism.

In the disclosure, the driving part arranged on both sides of the driving end drives the guide wire driving end to move forward or backward relative to the guide wire driven end in the direction perpendicular to the pushing direction of the guide wire. The high precision load cell arranged on the connecting plate transmits a force change signal received in the process of rolling and clamping to the control end of the driving end of the propulsion mechanism. The control end of the driving end of the propulsion mechanism detects the change of the clamping force by comparing the value change of the feedback force, and adjusts the clamping degree of the guide wire according to the stressed condition, so that the robot adopts proper clamping force to complete the operation, and the operation can be carried out safely and reliably. Meanwhile, when the clamping force is abnormal (too much or too little), a doctor can be timely reminded through the control end of the driving end of the robot propulsion mechanism, and the control end is a safety protection device and helps the doctor to perform interventional surgery treatment better.

At the same time, the structure of the driving end in the disclosure is relatively simple, compact and stable. When the rolling part is subjected to the force in the clamping direction of the guide wire, the force is transmitted to the right-angle connecting plate through the U-shaped slot connector, the first slider and the first micro linear guide. The driving end high precision load cell only measures the axial force of the guide wire, that is, the push-pull force felt by the high precision load cell (that is, the friction on the guide wire), so as to judge the force change of the axial friction of the guide wire. It gives timely operation reminder to the doctor and protect the safety of patients. The disclosure adopts an indirect force measuring method, and solves the problem of inconvenient installation of guide wire and force measuring device.

BRIEF DESCRIPTION OF THE DRAWINGS

In order to explain the embodiments of the present disclosure or the technical solutions in the prior art more clearly, the following drawings that need to be used in the description of the embodiments or the prior art will be briefly introduced. Obviously, the drawings in the following description are only embodiments of the present disclosure. For those of ordinary skill in the art, other drawings can be obtained based on the drawings disclosed without creative work.

Figure 1:
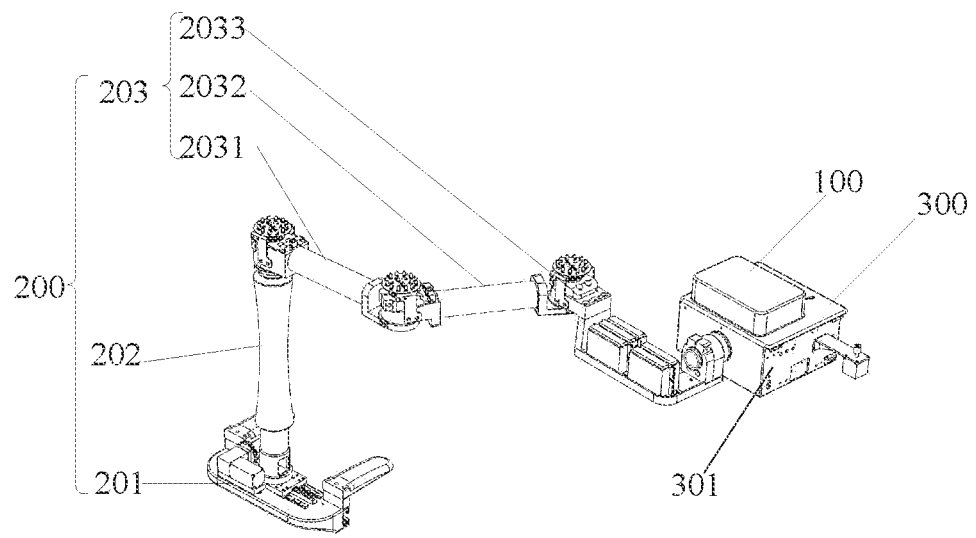
FIG. 1 is a structural diagram of universal robot for interventional angiographic surgery and interventional therapeutic surgery provided by the disclosure.
Figure 2:
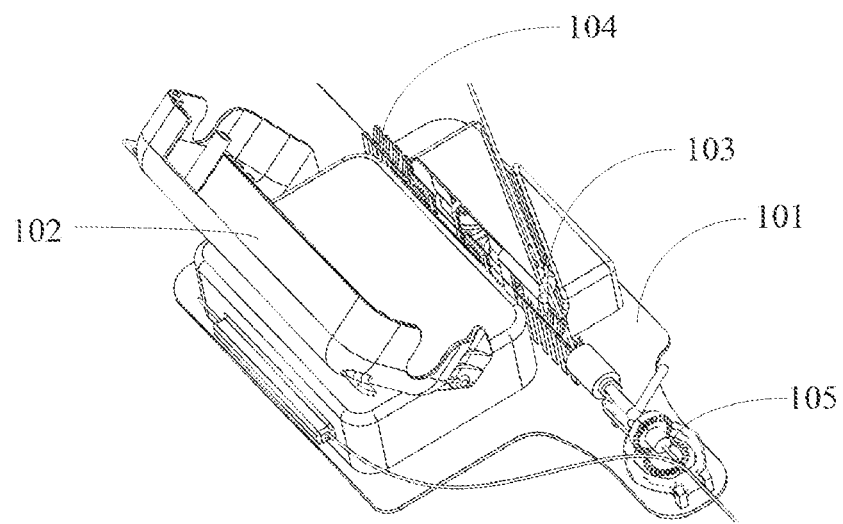
FIG. 2 is a structural diagram of the disinfection box.
Figure 3:
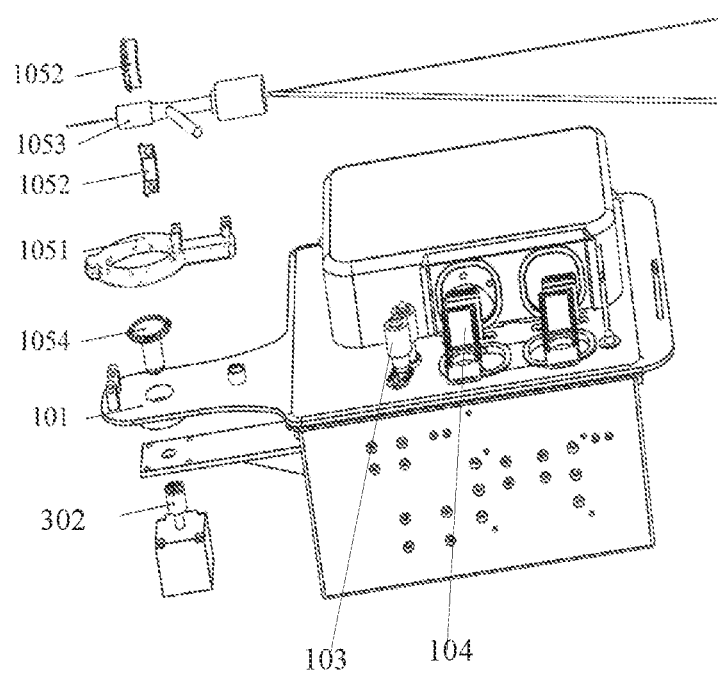
FIG. 3 and FIG. 4 is an exploded view of the Y-valve assembly of the disinfection box.
Figure 4:
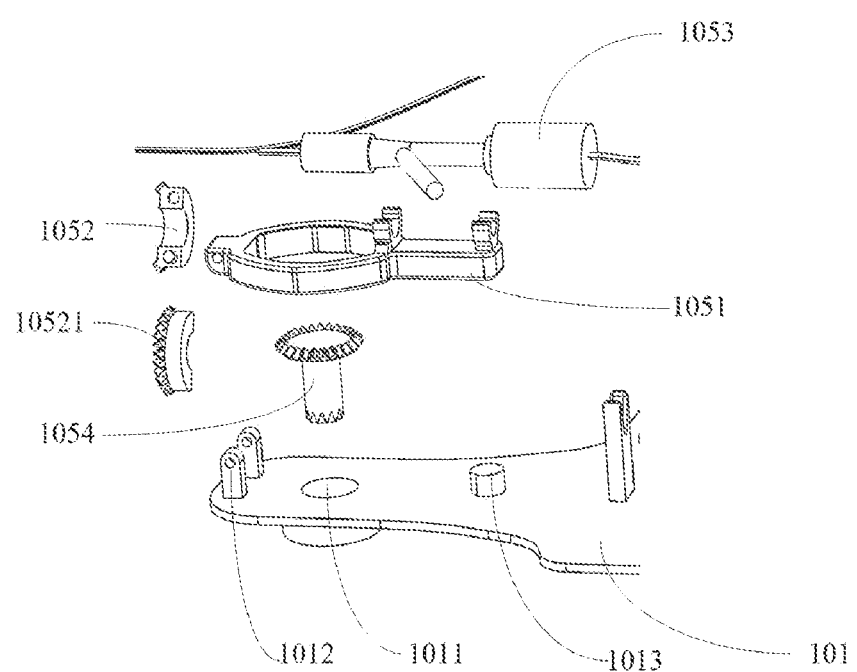

wherein, 100—disinfection box, 101—sterile box body, 1011—shaft hole, 1012—hinge block, 1013—first Y-valve electromagnet, 102—sterile box cover, 103—catheter control end, 104—guide wire rolling part, 1041—passive rolling part, 105—Y-valve assembly, 1051—Y-valve fixing member, 10511—engagement through hole, 10512—fixing plate, 10513—engaging ring body, 10514—claw, 10515—hinge, 1052—Y-valve holding member, 10521—toothed ring, 1053—Y-valve main body, 1054—Y-valve drive gear; 200—robot body, 201—base, 2011—column bottom plate, 2012—stoppers, 2013—cross braces, 2014—base rails, 2015—base sliders, 2016—rack, 2017—sliding groove, 202—column, 2021—connecting plate, 2022—base servo motor, 2023—base gear, 203—mechanical arm; 2031—rear arm, 20311—transverse shaft, 20312—first rotating shaft connecting assembly, 203121—first rotating shaft connector, 203122—first lubricating block, 203123—first bracket, 203124—first thread pressing cover, 203125—first shaft sleeve, 203126—limiting screw, 20313—rotating shaft fixing assembly, 203131—rotating shaft fixing part, 203132—wire pressing plate, 203133—transverse shaft limiting part, 203134—retaining ring, 203135—T-type thrust gasket, 20314—first rotating shaft, 2032—middle arm, 2033—forearm, 20331—front transverse plate, 20332—driver, 20333—inclined vertical plate, 20334—second rotating shaft connecting assembly, 203341—second rotating shaft connector, 203342—second lubricating block, 203343—second shaft sleeve, 203344—second bracket, 20335—forearm connecting shaft assembly, 203351—shaft support, 203352—third lubricating block, 203353—flange bearing, 203354—washer, 203355—second rotating shaft retaining ring, 20336—second rotating shaft;

300—propulsion mechanism, 301—shell, 302—motor output gear;

400—guide wire driving end, 401—U-shaped slot connector, 402—driving end high precision load cell, 403—first slider, 404—first micro linear guide, 405—right-angle connecting plate, 406—second slider, 407—second micro linear guide, 409—driving end connecting piece;

500—guide wire driven end, 501—driven end connecting plate, 502—driven end high precision load cell, 503—driven end micro linear guide, 504—driven end slider, 505—driven end connecting piece, 5011—upper connecting plate;

S—guide wire, T—camshaft.

DETAILED DESCRIPTION OF EMBODIMENTS

Hereinafter, embodiments of the present disclosure will be described in detail, embodiments of which are shown in the accompanying drawings, in which the same or similar elements or elements having the similar or similar functions are denoted by the same reference numerals throughout. The embodiments described below by reference to the accompanying drawings are exemplary and intended to explain the disclosure and should not be construed as limiting the disclosure.

In the description of the disclosure, it is to be understood that, the terms "up", "down", "front", "back", "left", "right", "vertical", "horizontal", "top", "bottom", "inside", "outside" etc., the orientation or positional relationship indicated is based on the shown in the drawings, merely to facilitate the description of the disclosure and to simplify the description, rather than indicating or implying that the devices or elements referred to must have a particular orientation, be constructed and operate in a specific orientation, and therefore it should not be construed as limiting the disclosure.

In addition, the term "first," "second" are used for descriptive purpose only and are not to be construed as indicating or implying relative importance or implicitly indicate the number of technical features indicated. Thus, a feature defined as "first" or "second" may include one or more of the features, either explicitly or implicitly. In the description of the present disclosure, "plural" means two or more than two, unless otherwise specifically defined.

In the present disclosure, unless otherwise expressly specified and defined, the terms "install," "connect," and "fix" are to be understood in a broad sense. For example, a fixed connection or a detachable connection, or in one piece; either mechanically or electrically connected; either directly or indirectly connected through an intermediate medium, either in communication between the two elements or in an interactive relationship between them. The specific meanings of the above terms in the present disclosure may be understood by those of ordinary skill in the art as the case may be.

In the present disclosure, unless otherwise expressly specified and defined, the first feature is "up" or "down" to the second feature may comprise the first and second features in direct contact; it is also possible to include the first and second features not in direct contact but by means of a further feature contact between them. In addition, that word "up", "above" and "on" of the first feature include the first feature being directly above and obliquely above the second feature, or simply indicate that the level of the first feature is higher than that of the second feature. If the first feature is "down", "below" and "under" the second feature includes the first feature being directly below and diagonally below the second feature, or simply indicating that the height of the first feature is less than the second feature.

Referring to FIG. 1-FIG. 5, the embodiment of the disclosure discloses a universal robot for interventional angiographic surgery and interventional therapeutic surgery including a robot body 200. The robot body 200 includes a base 201, a column 202 and a mechanical arm 203. A top of the base 201 is slidably connected with the column 202. A top of the column 202 is connected with the mechanical arm 203. A front end of the mechanical arm 203 is connected with a propulsion mechanism 300 and a disinfection box 100. The front end of the mechanical arm 203 supports the propulsion mechanism 300 and the disinfection box 100.

The disinfection box 100 includes a sterile box body 101 and a sterile box cover 102 hinged to one side of the sterile box body 101. A catheter drive assembly 103 and a guide wire drive assembly 104 are fixed on the sterile box body 101. A Y-valve assembly 105 is provided on one end of the sterile box body 101. The Y-valve assembly 105 includes a Y-valve fixing member 1051, a Y-valve holding member 1052, a Y-valve main body 1053 and a Y-valve drive gear 1054.

One end of the Y-valve fixing member 1051 is rotated on one end of the sterile box body 101 in an advancing direction of a catheter and a guide wire S. The other end of the Y-valve fixing member 1051 is magnetically connected with the sterile box body 101. An engagement through hole 10511 is provided in the middle of the Y-valve fixing member 1051. A shaft hole 1011 at a position corresponding to the engagement through hole 10511 is provided on the sterile box body 101. A bottom axle of the Y-valve drive gear 1054 is rotated in the shaft hole 1011, and the bottom of the axle is provided with an axle gear engaged with a motor output gear 107 in a propulsion mechanism. The Y-valve drive gear 1054 is provided in the engagement through hole 10511. The Y-valve holding member 1052 includes at least two sets of arc-shaped members connectable as a ring. A toothed ring 10521 meshed with Y-valve drive gear 1054 is provided on the ring. One end of the Y-valve main body 1053 is fixed in Y-valve holding member 1052 through an elastic filler, and the other end of the Y-valve main body 1053 is fixed on the Y-valve fixing member 1051.

The universal robot for interventional angiographic surgery and interventional therapeutic surgery disclosed in the present disclosure is provided with a changed structure of the Y-valve assembly thereof. Specially:

First, one end of Y-valve main body is fixed in the Y-valve holding member through an elastic filter. Through the deformation of the elastic filler, different specifications of the Y valve body can be used, so that different specification of the catheter or contrast catheter can be installed.

Second, the Y-valve driving gear is driven by the motor output gear in the propulsion mechanism, and the toothed ring on the Y-valve holding member can be driven at the same time, thus a universality of the interventional radiology and therapeutic operation disinfection box is realized.

Third, one end of a Y-valve fixing member is rotated on one side of the sterile box body in an advancing direction along a catheter and a guide wire, and the other end of the Y-valve fixing member is magnetically connected with the sterile box body, which allows the physician to replace the guide wire and catheter and fix the Y-valve main body.

The motor output gear drives the Y-valve drive gear, which in turn drives the toothed ring on the Y-valve holding member to further drives the angiography catheter to rotate. Forward and reverse rotation of the motor corresponds to clockwise and counter-clockwise rotation of the catheter respectively. The sterile box body is provided with a semi-closed hose, the inner diameter of the semi-closed hose is larger than the diameter of the catheter and can be sleeved on the outside of the angiography catheter, and the head of the hose is fixed on the outer sheath. When the advancement mechanism is moved as a whole, the angiography catheter can be moved along the hose into or out of the body.

The whole process of angiography surgery in the disclosure refers to the part with larger rays. The doctor needs to manually push the catheter and guide wire to the lesion. At this time, the robot will complete the rest of the fine operation. The robot in the disclosure also needs to cooperate with the disinfection box above the propulsion mechanism. The disinfection box is a sterile disposable product, so it can effectively solve the problem of difficult disinfection of surgical robot in clinical.

The sterile box cover can be rotated 150 degrees, with an electromagnet at the bottom for holding, and an open handle at the top. The elastic filler may be sponge, silica gel or the like.

Figure 5:
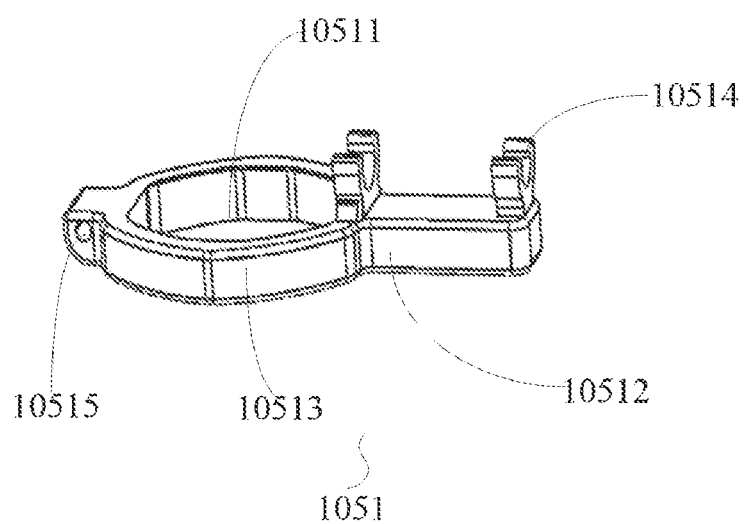
FIG. 5 is an enlarged view of the Y-valve assembly.

Referring to FIG. 5, the Y-valve fixing member 1051 includes a fixing plate 10512, an engaging ring body 10513, a hinge 10515 and a claw 10514. The fixing plate 10512 is bar shaped. A bottom of one end of the fixing plate 10512 is magnetically connected with the sterile box body 101. The other end of the fixing plate 10512 is integrally connected with one end of the engaging ring body 10513. The engagement through hole 10511 is formed in the middle of the engaging ring body 10513. The other end of the engagement ring body 10513 is connected with the hinge 10515. The hinge 10515 is hinged with a hinge block 1012 provided on the sterile box body 101 near an outside of the shaft hole 1011. At least two sets of the claw 10514 are sequentially arranged along a longitudinal direction of the fixing plate 10512. The other end of the Y-valve main body 1053 is engaged with the claw 10514. The claw has certain elasticity, and the top of the claw forms an opening, which is convenient for installation and disassembly. An inner side near the axle hole of the sterile box body is provided with a first Y-valve electromagnet. The first Y-valve electromagnet is magnetically connected with the corresponding second Y-valve electromagnet arranged on the position at the bottom of the fixing plate. Thus, the Y-valve body is conveniently fixed.

Figure 6:
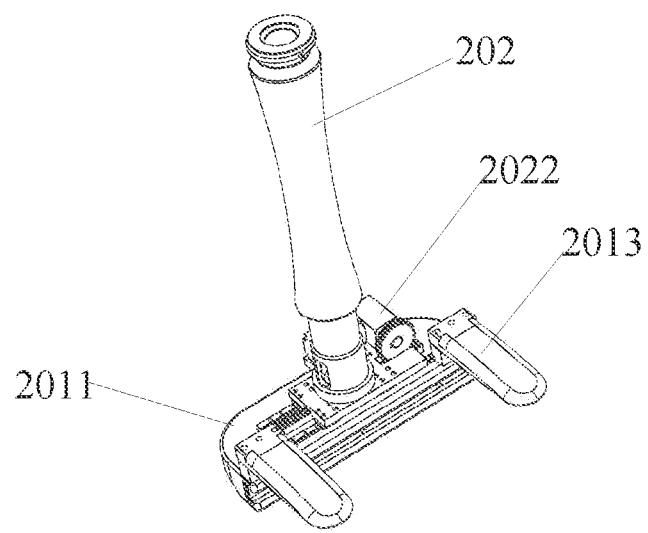
FIG. 6 is a structural diagram of the base and the column.
Figure 7:
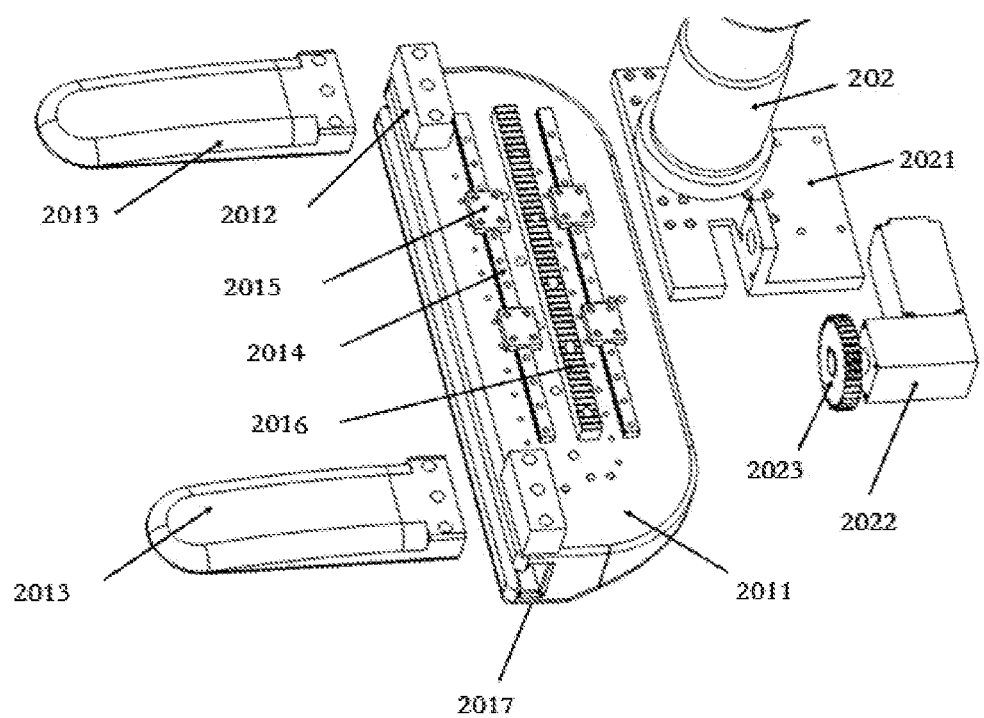
FIG. 7 is an exploded view of the base.

Referring to FIG. 6 and FIG. 7, in another embodiment of the disclosure, the base includes a column bottom plate 2011, a stopper 2012, a cross brace 2013, a base rail 2014, a base slider 2015, and a rack 2016. The stoppers 2012 are fixed on the column bottom plate 2011. The cross braces 2013 are fixed with the stopper 2012 and placed on a catheter bed. A top of the column bottom plate 2011 is fixed with the rack 2016 arranged along a length direction of the column bottom plate 2011. Two groups of the base rails 2014 are symmetrically arranged on both sides of the rack 2016, and each group of the base rails 2014 is slidably connected with the base sliders 2015. A bottom of the column 202 is provided with a connecting plate 2021. A bottom of the connecting plate 2021 is fixed on the base sliders 2015, and a top of the connecting plate 2021 is fixed with a base servo motor 2022. An output end of the base servo motor 2022 is provided with a base gear 2023 meshing with the rack 2016. The base servo motor drives the base gear and rack, and the column drives the mechanical arm and the propulsion mechanism to do translation motion, so as to drive the whole propulsion mechanism to move forward or backward. The imaging catheter is installed on the propulsion mechanism. The whole movement will drive the catheter into or out of the patient body, and then complete the process of angiography. Therefore, the reciprocating structure is adopted to reduce the space occupied by the operation of the equipment, which achieves the same effect as the doctor's actual interventional operation in a very small volume.

The stoppers also play the role of mechanical limit, which is used by matching with the connecting plate.

Referring to FIG. 7, a side of the column bottom plate 2011 close to the cross brace 2013 is provided with a sliding groove 2017 for inserting into a side guide rail of the catheter bed. There are tension screws at the bottom of the sliding groove for fixing. The bottom plate of the column is also provided with a wiring socket, which is used for connecting the power line and the communication line.

The two cross braces of the column can be placed on the catheter bed plate. The two cross braces, together with the sliding groove of the guide rail fixed on the catheter bed of the column, form a group of triangular stable structure. Thus, the stable connection between the mechanical arm and the catheter bed is ensured. The height of the column of the mechanical arm is appropriate, which ensures that it will not touch the patient and will not be too far away from the patient.

Referring to FIG. 8—FIG. 12, in an embodiment of the disclosure, the mechanical arm 203 includes a rear arm 2031, a middle arm 2032 and a forearm 2033 rotationally connected in turn. One end of the rear arm 2031 is rotationally connected to a top of the column 202. A front end of the forearm 2033 is connected with the propulsion mechanism 300 and the disinfection box 100. The front end of the forearm 2033 supports the propulsion mechanism 300 and the disinfection box 100. Each above rotating connection is provided with an annular indicator light respectively. The annular indicator lights display different colors according to different signals sent by the robot control circuit to feed back different state information of the robot. The mechanical arm is made of aluminum alloy, which is strong and light. The three straight arms are made of hollow aluminum profiles, which greatly reduces the weight of the mechanical arm.

Figure 8:
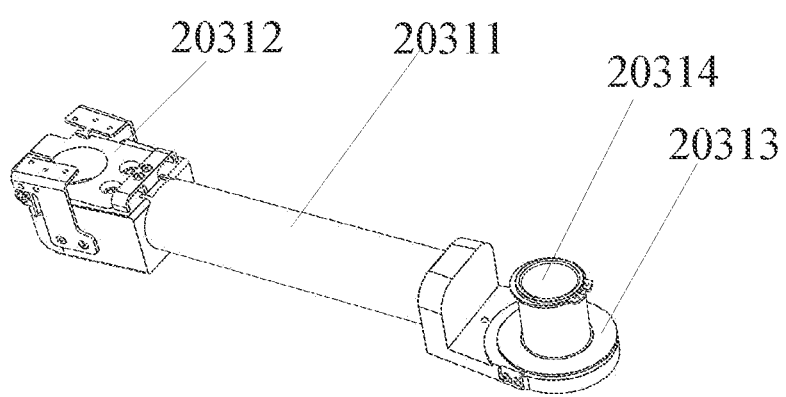
FIG. 8 is a structural diagram of the middle arm or the rear arm.
Figure 9:
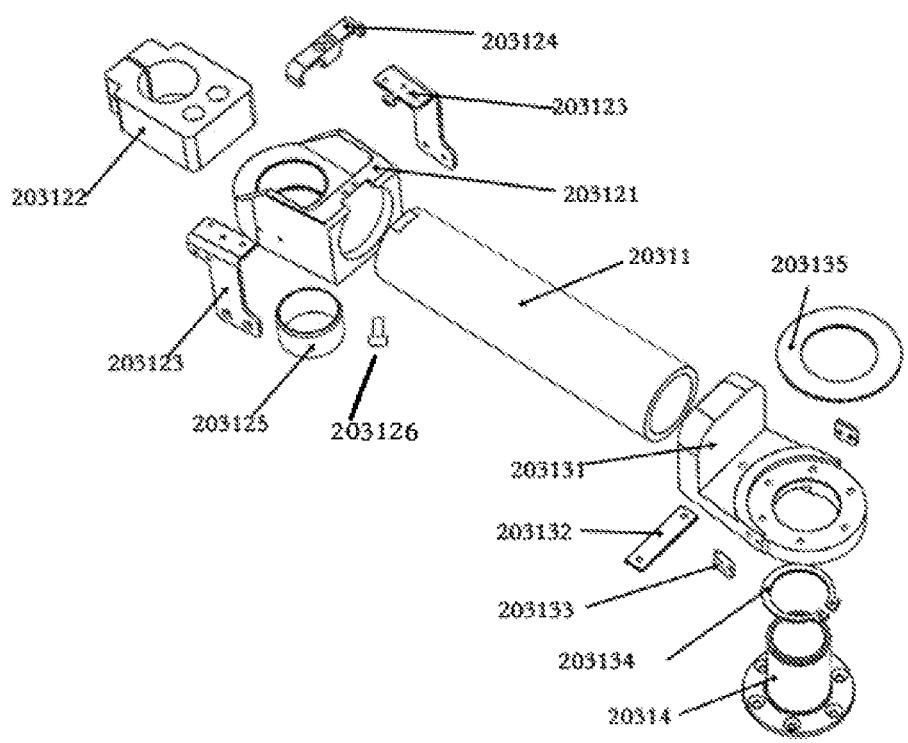
FIG. 9 is an exploded view of FIG. 8.
Figure 10:
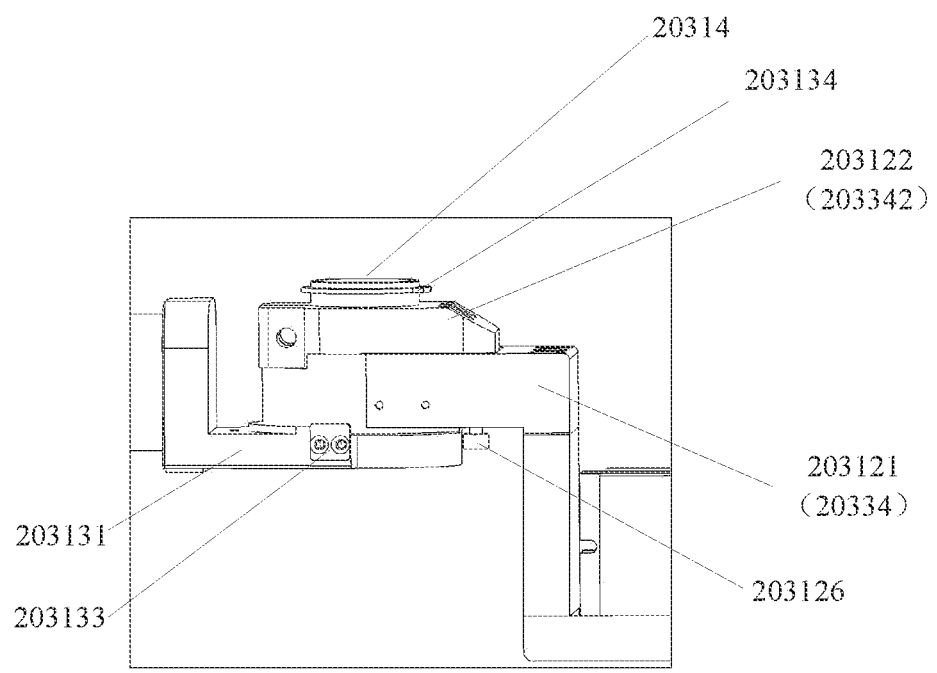
FIG. 10 is a diagram showing the connection of the rear arm and the middle arm.

Referring to FIG. 8-FIG. 10, specifically, the rear arm 2031 and the middle arm 2032 have a same structure, and both include a transverse shaft 20311, a first rotating shaft connecting assembly 20312, a rotating shaft fixing assembly 20313 and a first rotating shaft 20314. The first rotating shaft connecting assembly 20312 includes a first rotating shaft connector 203121, a first lubricating block 203122, a first bracket 203123, a first thread pressing cover 203124 and a first shaft sleeve 203125. One end of the first rotating shaft connector 203121 is fixed with one end of the transverse shaft 20311. A groove is formed on the first rotating shaft connector to accommodate the first lubricating block 203122. The first shaft sleeve 203125 penetrates through the through hole in the middle of the first s rotating haft connector 203121 and the first lubricating block 203122. Two first brackets 203123 for installing the annular indicator lights are symmetrically fixed on both sides of the first rotating shaft connector 203121. The first thread pressing cover 203124 is fixed on the first rotating shaft connector 203121 for fixing cables; the rotating shaft fixing assembly 20313 includes a rotating shaft fixing part 203131, a wire pressing plate 203132, a transverse shaft limiting part 203133, a retaining ring 203134 and a T-type thrust gasket 203135. One end of the rotating shaft fixing part 203131 forms a vertically arranged boss to fix the other end of the transverse shaft 20311. The boss is far away from the transverse shaft 20311 to form a shaft installation area vertically arranged with the boss. The shaft installation area is provided with the first rotating shaft 20314 through bolts. The T-type thrust gasket 203135 is arranged between a top of the fixing seat of the first rotating shaft 20314 and a matched group of the first shaft sleeves 203125. A top of the T-type thrust gasket 203135 is fixed by the retaining ring 203134. A top of the rotating shaft fixing part 203131 is provided with the wire pressing plate 203132 for fixing the cables. Two groups of the transverse shaft limiting parts 203133 provided on both sides of the rotating shaft fixing part 203131 and a limiting screw 203126 provided at a bottom of the first rotating shaft connector 203121 matched with the transverse shaft limiting parts 203133 form a stop mechanism for limiting the rotation of the transverse shaft 20311.

FIG. 10 shows a connection diagram of the rear arm and the middle arm. In the disclosure, the connection mode of the rear arm and the top of the column, the middle arm and the forearm is the same as that of the rear arm and the middle arm.

Figure 11:
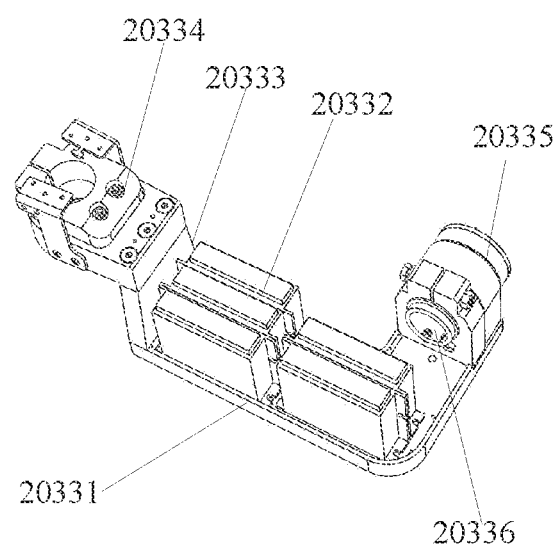
FIG. 11 is a structural diagram of the forearm.

Referring to FIG. 11, specifically, the forearm 2033 includes a front transverse plate 20331, a driver 20332, an inclined vertical plate 20333, a second rotating shaft connecting assembly 20334, a forearm connecting shaft assembly 20335 and a second rotating shaft 20336. A top of the front transverse plate 20331 is fixed with the driver 20332 for driving a stepper motor in the propulsion mechanism 300, and one end of the front transverse plate 20331 is fixedly connected with the second rotating shaft connecting assembly 20334 through the inclined vertical plate 20333. The second shaft connecting assembly 20334 is internally connected with the first rotating shaft 20314. The other end of the front transverse plate 20331 is fixed with the forearm connecting shaft assembly 20335. The second rotating shaft 20336 is matched with the forearm connecting shaft assembly 20335 and fixed on the propulsion mechanism 300.

Figure 12:
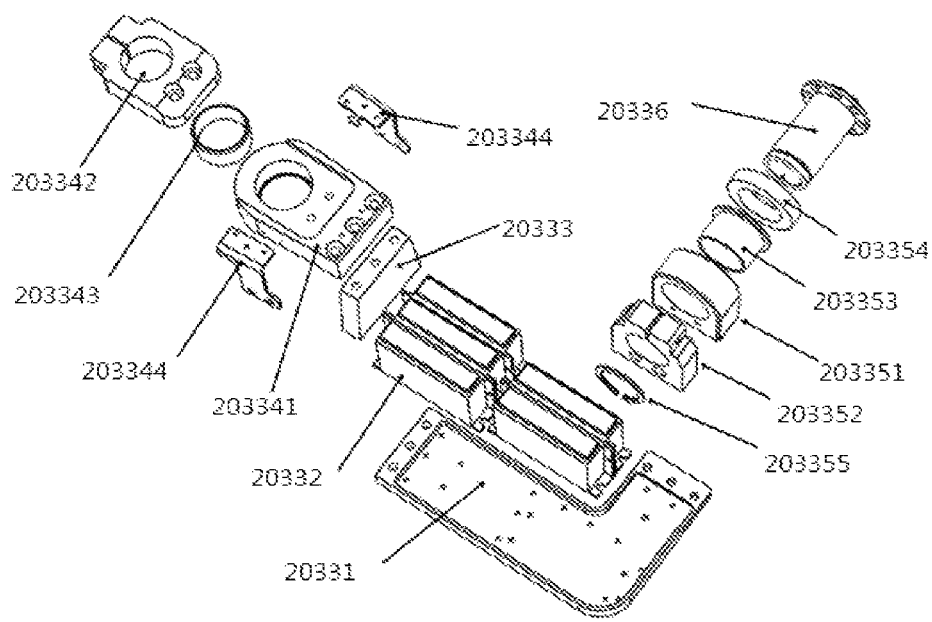
FIG. 12 is an exploded view of FIG. 10.

Referring to FIG. 12, the second shaft connecting assembly 20334 includes a second rotating shaft connector 203341, a second lubricating block 203342, a second shaft sleeve 203343 and a second bracket 203344. One end of the second rotating shaft connector 203341 is fixed on a top of the inclined vertical plate 20333 by a screw, and a holding groove is formed inside the second shaft connector 203341 for holding the second lubricating block 203342. The second shaft sleeve 203343 penetrates through the through hole in the middle of the second rotating shaft connector 203341 and the second lubricating block 203342. Two second brackets 203344 are fixed on both sides of the second rotating shaft connector 203341 for installing an annular indicator light. The forearm connecting shaft assembly 20335 includes a shaft support 203351, a third lubricating block 203352, a flange bearing 203353, a washer 203354 and a second rotating shaft retaining ring 203355. The shaft support 203351 is fixed on the front transverse plate 20331. The third lubricating block 203352 is fixed on one side of the shaft support 203351. The second rotating shaft 20336 is fixed on a side wall of the propulsion mechanism 300. The second rotating shaft 20336, the washer 203354, the flange bearing 203353 and the second rotating shaft retaining ring 203355 are matched and installed on the shaft support 203351, so that the propulsion mechanism 300 rotates along the shaft support 203351. The propulsion mechanism 300 can rotate along the shaft support 203351, so that a small rotation can meet the clinical needs.

Figure 13:
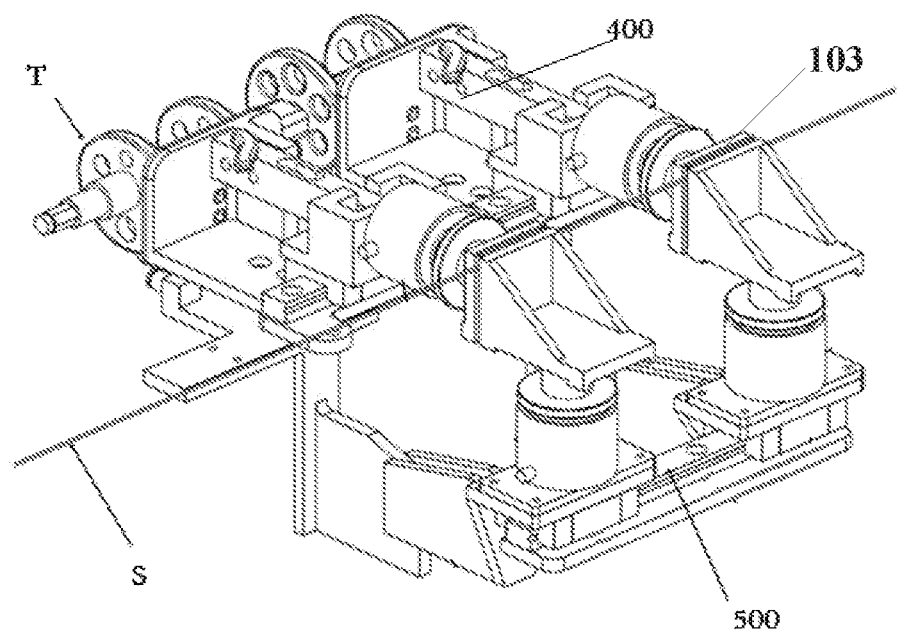
FIG. 13 shows the guide wire driving end and the guide wire driven end.

Referring to FIG. 1 and FIG. 13, in other embodiments of the disclosure, the propulsion mechanism 300 includes a shell 301, a guide wire driving end 400, a guide wire driven end 500 and a catheter control end 103. One side of the shell 301 is rotationally connected with the mechanical arm 203. An inner part of the shell 301 is used to support and accommodate a guide wire driving end 400, a guide wire driven end 500 and a catheter control end 103. The disinfection box 100 is magnetically connected with a top of the shell 301. A top of the catheter control end 103 penetrates into the disinfection box 100. The guide wire driving end 400 and the guide wire driven end 500 are symmetrically arranged along the guide wire S. A side of the guide wire driving end 400 close to the guide wire S and a side of the guide wire driven end 500 close to the guide wire S are connected with two groups of matching guide wire rolling parts 104 respectively.

Figure 14:
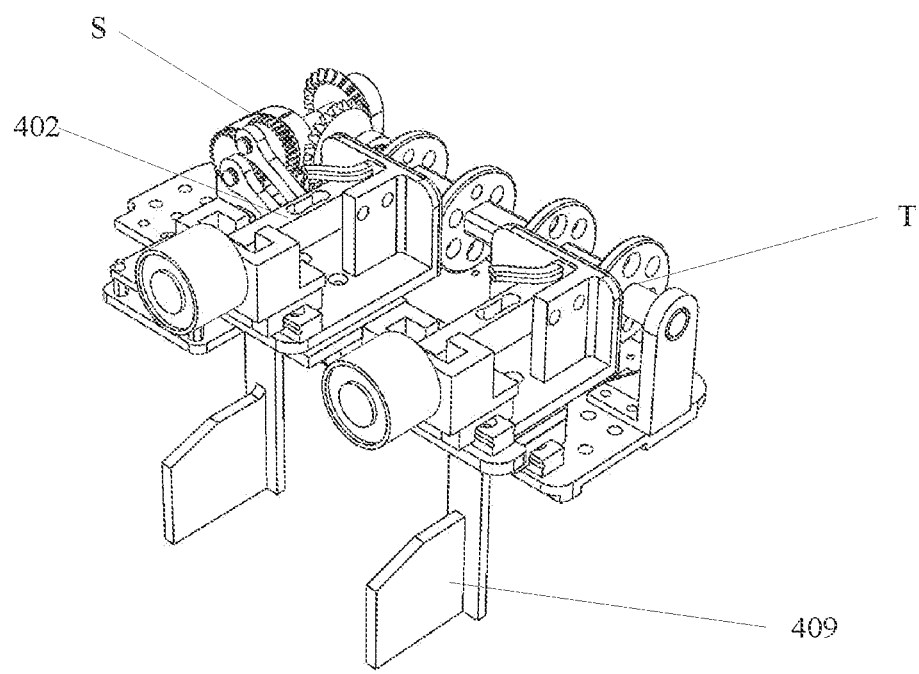
FIG. 14 and FIG. 15 are structural diagrams of the guide wire driving end.
Figure 15:
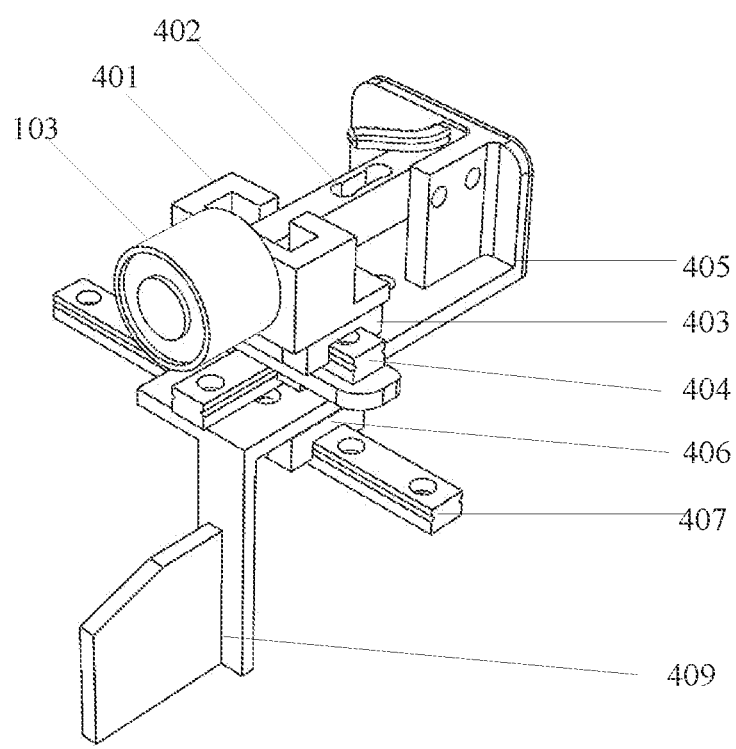

Referring to FIG. 14 and FIG. 15, advantageously, the guide wire driving end 400 includes a driving end connecting plate and two groups of driving end parts. Each set of the driving end part includes a U-shaped slot connector 401, a driving end high precision load cell 402, a first slider 403, a first micro linear guide 404, a right-angle connecting plate 405 and a driving end connecting piece 409. A top of the driving end connecting piece 409 slides along a direction parallel to the guide wire S on a length direction of the driving end connecting piece. A bottom of the right-angle connecting plate 405 slides perpendicularly to the direction of the guide wire S on the top of the driving end connecting piece 409. An outside of a vertical plate connected on one end of the right-angle connecting plate 405 is butted with a camshaft T, and a top of the other end is fixed with the first micro linear guide 404 parallel to the direction of the guide wire S. The first slider 203 slides on the first micro linear guide 404, and the U-shaped slot connector 401 is fixed on the top of the first slider 403 to counteract a clamping force of the guide wire S. The driving end high precision load cell 402 is arranged perpendicularly to the guide wire S. One end of the driving end high precision load cell 402 is fixed on an inner side of the vertical plate, and the other end is inserted into a notch of the U-shaped slot connector 401, and a width of the notch is greater than a width of the driving end high precision load cell 402. The high precision load cell 402 is used to measure a friction on the guide wire S. A side far away from the notch of the U-shaped slot connector 401 is fixed with one end of a first clamping part.

In the disclosure, the driving part arranged on both sides of the driving end drives the guide wire driving end to move forward or backward relative to the guide wire driven end in the direction perpendicular to the pushing direction of the guide wire. The high precision load cell arranged on the connecting plate transmits a force change signal received in the process of rolling and clamping to the control end of the driving end of the propulsion mechanism. The control end of the driving end of the propulsion mechanism detects the change of the clamping force by comparing the value change of the feedback force, and adjusts the clamping degree of the guide wire according to the stressed condition, so that the robot adopts proper clamping force to complete the operation, and the operation can be carried out safely and reliably. Meanwhile, when the clamping force is abnormal (too much or too little), a doctor can be timely reminded through the control end of the driving end of the robot propulsion mechanism, and the control end is a safety protection device and helps the doctor to perform interventional surgery treatment better.

In the disclosure, the precision of the high precision load cell is less than or equal to 0.01N.

The guide wire driving end further includes a second slider 406 and a second micro linear guide 407. The bottom of the right-angle connecting plate 405 is fixed with the second slider 406 along a vertical direction with the guide wire S, and the top of the driving end connecting piece 409 is provided with the second micro linear guide 407 sliding with the second slider 406.

The guide wire driving end further includes a spring and a polytetrafluoro patch. Two ends of the spring are respectively hooked and fixed between the outer side of the vertical plate and the polytetrafluoro patch. The polytetrafluoro patch is always butted with the camshaft T.

Figure 16:
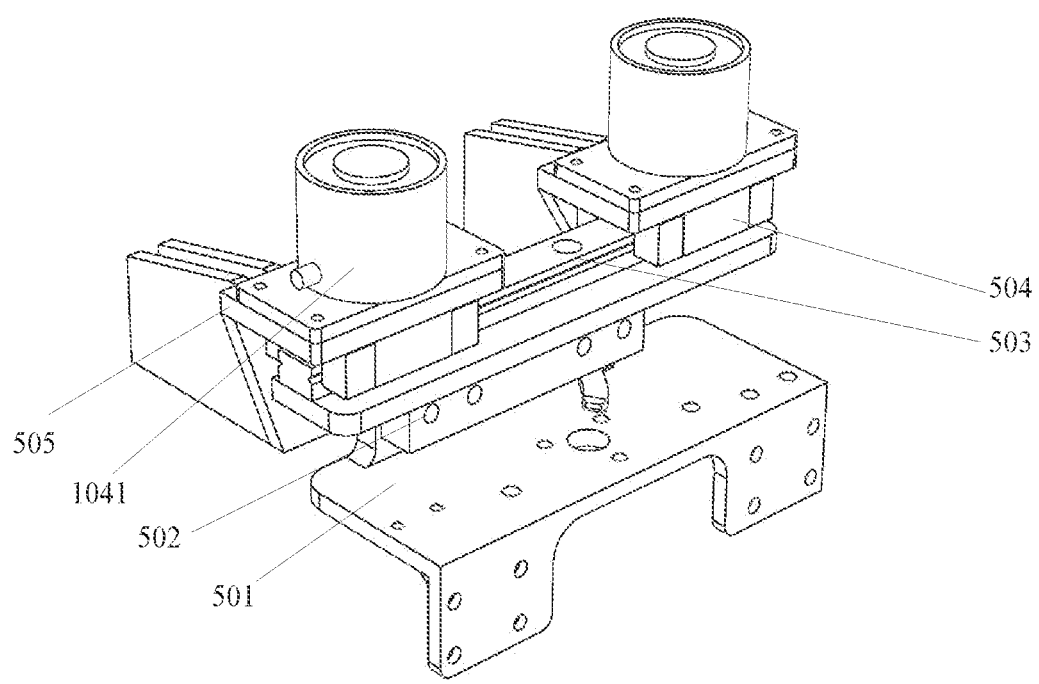
FIG. 16 and FIG. 17 are structural diagrams of the guide wire driven end.
Figure 17:
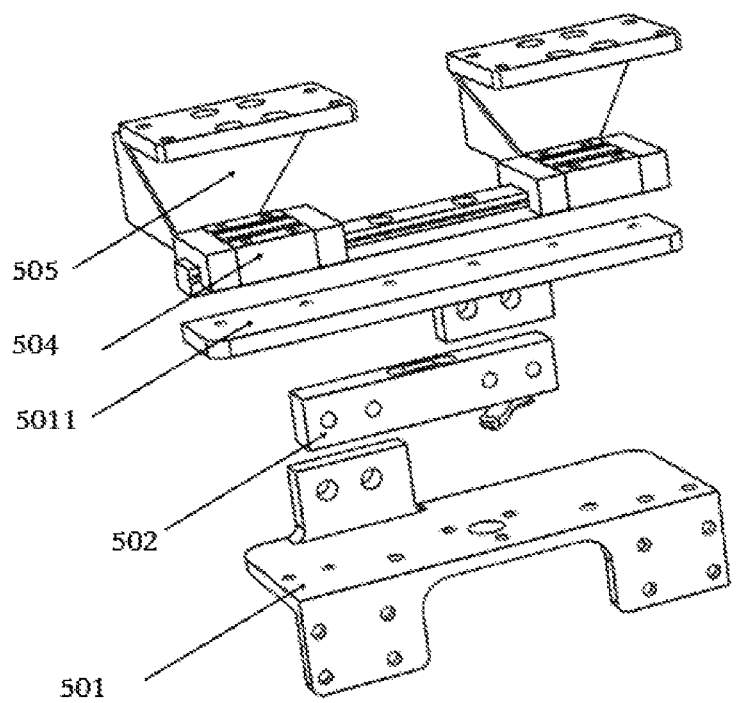

Referring to FIG. 16 and FIG. 17, more advantageously, the guide wire driven end 500 includes a driven end connecting plate 501, a driven end high precision load cell 502, a driven end micro linear guide 503, a driven end slider 504, a driven end connecting piece 505 and two groups of passive rolling parts 1041. A side surface of the driven end connecting plate 501 close to the guide wire S is fixed with the driven end high precision load cell 502. A top of the driven end connecting plate 501 is fixed with the driven end micro linear guide 503. Two driven end connecting piece 505 are fixed on the tops of the two driven end sliders 504 and slide on the driven end micro linear guide 503. A top of each driven end connecting piece 505 is fixedly provided with the passive rolling part 1041 matched with an active rolling part of the guide wire driving end 400 respectively. The driven end high precision load cell 502 transmits a force change signal received in the process of rolling and clamping to a control end of the driving end of the propulsion mechanism. Where, the driven end connecting plate 501 includes a lower connecting plate and an upper connecting plate 5011. The lower connecting plate includes an integrally connected horizontal plate and a vertical plate, and the top of the horizontal plate is provided with a first sensor fixing plate on the side close to the guide wire. The second sensor fixing plate arranged staggered from the first sensor fixing plate is provided on the side close to the guide wire at the bottom of the upper connecting plate. The first sensor fixing plate and the second sensor fixing plate have the same size and are all provided with a first mounting hole. The high precision load cell is provided with a second mounting hole corresponding to the position of the first mounting hole. The first mounting hole and the second mounting hole are fixed by bolts.

The structure of the driving end in the disclosure is relatively simple, compact and stable. When the rolling part is subjected to the force in the clamping direction of the guide wire, the force is transmitted to the right-angle connecting plate through the U-shaped slot connector, the first slider and the first micro linear guide. The driving end high precision load cell only measures the axial force of the guide wire, that is, the push-pull force felt by the high precision load cell that is, the friction on the guide wire, so as to judge the force change of the axial friction of the guide wire. It gives timely operation reminder to the doctor and protect the safety of patients. The disclosure adopts an indirect force measuring method, and solves the problem of inconvenient installation of guide wire and force measuring device.

In the present disclosure, the driving end, the driven end and the guide wire rolling part have two sets of left and right sides, their shapes and sizes are the same, and the functions are the same, but they work at different positions and timings. The device is used in the reciprocating propulsion mechanism and has two groups of clamping parts to clamp the guide wire. Under the cooperation of the camshaft and gear transmission group (the structure of the gear transmission group is shown in patent document 201911259494.4), two connecting rods in the gear transmission group are respectively connected with two sets of the driving end connecting pieces to drive two sets of driving end parts to slide along the length of rectangular bottom plate, and then complete the clamping and propulsion with the clamping parts of the driven end parts. Four cams are provided on the camshaft, and the cams have a certain angle difference to ensure that at the same time, only one group of cams pushes the driving end part to make the guide wire clamper to clamp the guide wire. Therefore, only when the guide wire is clamped, the tactile force feedback device (the high precision load cell) can collect the signal, and when the guide wire is loosened, it does not need to collect the signal of the sensor. The passive movable block at the driven end of the propulsion mechanism is used to assist in tightening the guide wire. The polytetrafluoro patch is adhered to the right-angle connecting plate. Under the action of the spring, the polytetrafluoro patch always fits with the camshaft. When a group of active movable blocks and passive movable blocks clamp the guide wire, and the first electromagnet receives the force in the clamping direction of the guide wire, the force is transmitted to the right-angle connecting plate through the U-shaped slot connector, the first slider and the first micro linear guide. The high precision load cell only measures the force along the axial direction of the guide wire, that is, the friction on the guide wire.

The guide wire friction feedback device for interventional surgical robot is used in conjunction with a reciprocating motion device of the interventional surgery robot. Two sets of the clamping parts clamp alternately and move the guide wire during the reciprocating motion of the guide wire. The friction force in a motion of the guide wire is measured by detecting a force change signal from the high precision load cell to indirectly reflect the force on a guide wire end. A data is transmitted to a control end of the driving end of the propulsion mechanism of the robot to give timely feedback to the doctor.

During the process of rolling and clamping, the high precision load cell receives the force change and feeds it back to the control end of the propulsion mechanism, and the control end of the propulsion mechanism detects the clamping force by comparing the feedback force value change, and adjusts the driving part to change the clamping force according to the needs of use. The precision of the high precision load cell is less than or equal to 0.01N load cell. The high precision load cell has proper size and high sensitivity. When the moving block clamps the guide wire, a small change can be brought to the highly precise load cell in the transmission of each component. In the control end of the driving end of the propulsion mechanism, the clamping force is detected by comparing the numerical value change of the high precision load cell. The two ends of the high precision load cell are respectively fixed with the upper connecting plate and the lower connecting plate, wherein the upper connection plate is provided with a driving micro linear guide rail and a secondary end electromagnet, and the lower connection plate can be fixed through the guide rails and a housing. The driving end clamping the guide wire is matched with the high precision weight load cell to realize the action of a stepper motor, so that the clamping force of the guide wire can be controlled. That is, the motor rotates forward, the driving end moves forward as a whole, and the movable block attracted by the electromagnet at the driving end is driven to move forwards and the movable block is close to the movable block of the driven end, so that the clamping force of the guide wire is increased. Conversely, the motor reverses rotation and the clamping force decreases.

The guide wire clamping force control device can adjust the clamping force when initialization is carried out after the guide wire is placed. The clamping force can be set by user, and the clamping force can be adjusted according to the actual situation. Moreover, the change of the clamping force can be observed at any time during operation, and the clamping force can be adjusted at any time when necessary, so that the clamping device is more flexible in practical use.

The rolling part of the disclosure refers to the patent document CN201911213936.1.

Therefore, the disclosure solves the problems existing in the existing interventional surgery robot, such as the inability to complete the two processes of interventional surgery at the same time, the lack of force detection for the axial friction force of guide wire, the difficulty in installing the force detection device, the inability to meet the clinical needs, the complex structure of the robot in the actual surgery, the too large volume, and so on. The disclosure provides help for the robot to simulate the alternating operation of the hands of the doctor. The robot can meet the needs of both angiographic surgery and therapeutic surgery, which greatly facilitates the clinical use. The robot has the advantages of simple structure, good stability, modular structure design, simple assembly and disassembly, compact structure and small volume, which is very suitable for the operation environment. By measuring the push and pull force of the micro force sensor at the driving end, the change of the axial friction force of the guide wire can be judged, which can give the doctor timely operation reminder and protect the safety of patients. According to the feedback value of the high precision load cell at the driven end, the clamping degree of the guide wire can be adjusted at any time to ensure that there is no slipping phenomenon, which can meet the needs of vascular interventional surgery.

In the description of the present specification, reference to the description of the terms "one embodiment", "some embodiments", "an example", "a specific example", or "some examples" or the like, is intended to refer to specific features, structures, materials or features that are included in at least one embodiment or example of the disclosure. In the specification, the schematic representations of the above terms are not necessarily directed to the same embodiments or examples. Moreover, the particular features, structures, materials, or features described may be combined in any one or more embodiments or examples in a suitable manner. In addition, those skilled in the art may join and combine the different embodiments or examples described in this specification.

Although the embodiments of the present disclosure have been shown and described above, it is to be understood that the embodiments described above are exemplary and not to be construed as limiting the disclosure. Variations, modifications, substitutions, and variations of the above-described embodiments may be made by one of ordinary skill in the art within the scope of the present disclosure.

What is claimed is:

1. A general robot for interventional angiographic surgery and interventional therapeutic surgery, comprising a robot body (200); wherein the robot body (200) comprises a base (201), a column (202) and a mechanical arm (203); a top of the base (201) is slidably connected with the column (202); a top of the column (202) is connected with the mechanical arm (203); a front end of the mechanical arm (203) is connected with a propulsion mechanism (300) and a disinfection box (100); and the front end of the mechanical arm (203) supports the propulsion mechanism (300) and the disinfection box (100);

the disinfection box (100) comprises a sterile box body (101) and a sterile box cover (102) hinged to one side of the sterile box body (101); a catheter drive assembly (103) and a guide wire drive assembly (104) are fixed on the sterile box body (101); a Y-valve assembly (105) is provided on one end of the sterile box body (101); the Y-valve assembly (105) comprises a Y-valve fixing member (1051), a Y-valve holding member (1052), a Y-valve main body (1053) and a Y-valve drive gear (1054);

one end of the Y-valve fixing member (1051) is rotated on one end of the sterile box body (101) in an advancing direction of a catheter and a guide wire (S); an other end of the Y-valve fixing member (1051) is magnetically connected with the sterile box body (101); an engagement through hole (10511) is provided in the middle of the Y-valve fixing member (1051); a shaft hole (1011) at a position corresponding to the engagement through hole (10511) is provided on the sterile box body (101); a bottom axle of the Y-valve drive gear (1054) is rotated in the shaft hole (1011), and the bottom of the axle is provided with an axle gear engaged with a motor output gear (107) in the propulsion mechanism; the Y-valve drive gear (1054) is provided in the engagement through hole (10511); the Y-valve holding member (1052) comprises at least two sets of arc-shaped members connectable as a ring; a toothed ring (10521) meshed with Y-valve drive gear (1054) is provided on the ring; and one end of the Y-valve main body (1053) is fixed in Y-valve holding member (1052) through an elastic filler, and an other end of the Y-valve main body (1053) is fixed on the Y-valve fixing member (1051).

2. The general robot for interventional angiographic surgery and interventional therapeutic surgery of claim 1, wherein the Y-valve fixing member (1051) comprises a fixing plate (10512), an engaging ring body (10513), a hinge (10515) and a claw (10514); the fixing plate (10512) is bar shaped; a bottom of one end of the fixing plate (10512) is magnetically connected with the sterile box body (101); an other end of the fixing plate (10512) is integrally connected with one end of the engaging ring body (10513); the engagement through hole (10511) is formed in the middle of the engaging ring body (10513); the other end of the engagement ring body (10513) is connected with the hinge (10515); the hinge (10515) is hinged with a hinge block (1012) provided on the sterile box body (101) near an outside of the shaft hole (1011); at least two sets of the claw (10514) are sequentially arranged along a longitudinal direction of the fixing plate (10512); and the other end of the Y-valve main body (1053) is engaged with the claw (10514).

3. The general robot for interventional angiographic surgery and interventional therapeutic surgery of claim 1, wherein the base (201) comprises a column bottom plate (2011), a stopper (2012), a cross brace (2013), a base rail (2014), a base slider (2015), and a rack (2016); the stoppers (2012) are fixed on the column bottom plate (2011); the cross braces (2013) are fixed with the stopper (2012) and placed on a catheter bed; a top of the column bottom plate (2011) is fixed with the rack (2016) arranged along a length direction of the column bottom plate (2011); two groups of the base rails (2014) are symmetrically arranged on both sides of the rack (2016), and each group of the base rails (2014) is slidably connected with the base sliders (2015); a bottom of the column (202) is provided with a connecting plate (2021); a bottom of the connecting plate (2021) is fixed on the base sliders (2015), and a top of the connecting plate (2021) is fixed with a base servo motor (2022); and an output end of the base servo motor (2022) is provided with a base gear (2023) meshing with the rack (2016).

4. The general robot for interventional angiographic surgery and interventional therapeutic surgery of claim 3, wherein a side of the column bottom plate (2011) close to the cross brace (2013) is provided with a sliding groove (2017) for inserting into a side guide rail of the catheter bed.

5. The general robot for interventional angiographic surgery and interventional therapeutic surgery of claim 3, wherein the mechanical arm (203) comprises a rear arm (2031), a middle arm (2032) and a forearm (2033) rotationally connected in turn; one end of the rear arm (2031) is rotationally connected to a top of the column (202); a front end of the forearm (2033) is connected with the propulsion mechanism (300) and the disinfection box (100); the front end of the forearm (2033) supports the propulsion mechanism (300) and the disinfection box (100); each above rotating connection is provided with an annular indicator light respectively; and the annular indicator lights display different colors according to different signals sent by the robot control circuit to feed back different state information of the robot.

6. The general robot for interventional angiographic surgery and interventional therapeutic surgery of claim 5, wherein the rear arm (2031) and the middle arm (2032) have a same structure, and both include a transverse shaft (20311), a first rotating shaft connecting assembly (20312), a rotating shaft fixing assembly (20313) and a first rotating shaft (20314); the first rotating shaft connecting assembly (20312) comprises a first rotating shaft connector (203121), a first lubricating block (203122), a first bracket (203123), a first thread pressing cover (203124) and a first shaft sleeve (203125); one end of the first rotating shaft connector (203121) is fixed with one end of the transverse shaft (20311); a groove is formed on the first rotating shaft connector to accommodate the first lubricating block (203122); the first shaft sleeve (203125) penetrates through the through hole in the middle of the first s rotating haft connector (203121) and the first lubricating block (203122); two first brackets (203123) for installing the annular indicator lights are symmetrically fixed on both sides of the first rotating shaft connector (203121); the first thread pressing cover (203124) is fixed on the first rotating shaft connector (203121) for fixing cables; the rotating shaft fixing assembly (20313) comprises a rotating shaft fixing part (203131), a wire pressing plate (203132), a transverse shaft limiting part (203133), a retaining ring (203134) and a T-type thrust gasket (203135); one end of the rotating shaft fixing part (203131) forms a vertically arranged boss to fix an other end of the transverse shaft (20311); the boss is far away from the transverse shaft (20311) to form a shaft installation area vertically arranged with the boss; the shaft installation area is provided with the first rotating shaft (20314) through bolts; the T-type thrust gasket (203135) is arranged between a top of the fixing seat of the first rotating shaft (20314) and a matched group of the first shaft sleeves (203125); a top of the T-type thrust gasket (203135) is fixed by the retaining ring (203134); a top of the rotating shaft fixing part (203131) is provided with the wire pressing plate (203132) for fixing the cables; and two groups of the transverse shaft limiting parts (203133) provided on both sides of the rotating shaft fixing part (203131) and a limiting screw (203126) provided at a bottom of the first rotating shaft connector (203121) matched with the transverse shaft limiting parts (203133) form a stop mechanism for limiting the rotation of the transverse shaft (20311).

7. The general robot for interventional angiographic surgery and interventional therapeutic surgery of claim 6, wherein the forearm (2033) comprises a front transverse plate (20331), a driver (20332), an inclined vertical plate (20333), a second rotating shaft connecting assembly (20334), a forearm connecting shaft assembly (20335) and a second rotating shaft (20336); a top of the front transverse plate (20331) is fixed with the driver (20332) for driving a stepper motor in the propulsion mechanism (300), and one end of the front transverse plate (20331) is fixedly connected with the second rotating shaft connecting assembly (20334) through the inclined vertical plate (20333); the second shaft connecting assembly (20334) is internally connected with the first rotating shaft (20314); an other end of the front transverse plate (20331) is fixed with the forearm connecting shaft assembly (20335); the second rotating shaft (20336) is matched with the forearm connecting shaft assembly (20335) and fixed on the propulsion mechanism (300).

8. The general robot for interventional angiographic surgery and interventional therapeutic surgery of claim 7, wherein the second shaft connecting assembly (20334) comprises a second rotating shaft connector (203341), a second lubricating block (203342), a second shaft sleeve (203343) and a second bracket (203344); one end of the second rotating shaft connector (203341) is fixed on a top of the inclined vertical plate (20333) by a screw, and a holding groove is formed inside the second shaft connector (203341) for holding the second lubricating block (203342); the second shaft sleeve (203343) penetrates through the through hole in the middle of the second rotating shaft connector (203341) and the second lubricating block (203342); two second brackets (203344) are fixed on both sides of the second rotating shaft connector (203341) for installing an annular indicator light; the forearm connecting shaft assembly (20335) comprises a shaft support (203351), a third lubricating block (203352), a flange bearing (203353), a washer (203354) and a second rotating shaft retaining ring (203355); the shaft support (203351) is fixed on the front transverse plate (20331); the third lubricating block (203352) is fixed on one side of the shaft support (203351); the second rotating shaft (20336) is fixed on a side wall of the propulsion mechanism (300); and the second rotating shaft (20336), the washer (203354), the flange bearing (203353) and the second rotating shaft retaining ring (203355) are matched and installed on the shaft support (203351), so that the propulsion mechanism (300) rotates along the shaft support (203351).

9. The general robot for interventional angiographic surgery and interventional therapeutic surgery of claim 1, wherein the propulsion mechanism (300) comprises a shell (301), a guide wire driving end (400), a guide wire driven end (500) and a catheter control end (103); one side of the shell (301) is rotationally connected with the mechanical arm (203); an inner part of the shell (301) is used to support and accommodate the guide wire driving end (400), the guide wire driven end (500) and the catheter control end (103); the disinfection box (100) is magnetically connected with a top of the shell (301); a top of the catheter control end (103) penetrates into the disinfection box (100); the guide wire driving end (400) and the guide wire driven end (500) are symmetrically arranged along the guide wire (S); and a side of the guide wire driving end (400) close to the guide wire (S) and a side of the guide wire driven end (500) close to the guide wire (S) are connected with two groups of matching guide wire rolling parts (104) respectively.

10. The general robot for interventional angiographic surgery and interventional therapeutic surgery of claim 1, wherein the guide wire driving end (400) comprises a driving end connecting plate and two groups of driving end parts; each set of the driving end part comprises a U-shaped slot connector (401), a driving end high precision load cell (402), a first slider (403), a first micro linear guide (404), a right-angle connecting plate (405) and a driving end connecting piece (409); a top of the driving end connecting piece (409) slides along a direction parallel to the guide wire (S) on a length direction of the driving end connecting plate; a bottom of the right-angle connecting plate (405) slides perpendicularly to the direction of the guide wire (S) on the top of the driving end connecting piece (409); an outside of a vertical plate connected on one end of the right-angle connecting plate (405) is butted with a camshaft (T), and a top of the other end is fixed with the first micro linear guide (404) parallel to the direction of the guide wire (S); the first slider (203) slides on the first micro linear guide (404), and the U-shaped slot connector (401) is fixed on the top of the first slider (403) to counteract a clamping force of the guide wire (S); the driving end high precision load cell (402) is arranged perpendicularly to the guide wire (S); one end of the driving end high precision load cell (402) is fixed on an inner side of the vertical plate, and the other end is inserted into a notch of the U-shaped slot connector (401), and a width of the notch is greater than a width of the driving end high precision load cell (402); the high precision load cell (402) is used to measure a friction on the guide wire (S); a side far away from the notch of the U-shaped slot connector (401) is fixed with one end of a first clamping part;

the guide wire driven end (500) comprises a driven end connecting plate (501), a driven end high precision load cell (502), a driven end micro linear guide (503), a driven end slider (504), a driven end connecting piece (505) and two groups of passive rolling parts (1041); a side surface of the driven end connecting plate (501) close to the guide wire (S) is fixed with the driven end high precision load cell (502); a top of the driven end connecting plate (501) is fixed with the driven end micro linear guide (503); two driven end connecting piece (505) are fixed on the tops of the two driven end sliders (504) and slide on the driven end micro linear guide (503); a top of each driven end connecting piece (505) is fixedly provided with the passive rolling part (1041) matched with an active rolling part of the guide wire driving end (400) respectively; and the driven end high precision load cell (502) transmits a force change signal received in the process of rolling and clamping to a control end of the driving end of the propulsion mechanism.

* * * * *